United States Patent [19]

Phillips et al.

[11] Patent Number: 5,041,289

[45] Date of Patent: Aug. 20, 1991

[54] METHOD OF PURGING RESIDUAL TUMOR CELLS IN VITRO WITH LYMPHOKINE ACTIVATED CYTOTOXIC CELLS

[75] Inventors: Joseph H. Phillips, San Mateo; Arnon Nagler, Palo Alto; Lewis L. Lanier, Los Altos, all of Calif.

[73] Assignee: Becton Dickinson and Company, Franklin Lakes, N.J.

[21] Appl. No.: 120,299

[22] Filed: Nov. 13, 1987

[51] Int. Cl.$^5$ ............................................. A61K 39/00
[52] U.S. Cl. ............................ 424/85.2; 424/85.1; 424/85.4; 435/240.1; 435/240.2; 435/240.21
[58] Field of Search ................. 424/85.1, 85.2, 85.4; 514/21, 908; 435/240.1, 240.2, 240.21

[56] References Cited

U.S. PATENT DOCUMENTS 4,604,377  8/1986  Fernandes et al. ............... 530/351
4,690,915  9/1987  Rosenberg ............................ 514/2
4,714,680  12/1987  Civin .......................... 435/240.25

OTHER PUBLICATIONS

Sarh, *Suina* 238, 1987, pp. 1374–1379.
Suda et al., Blood 67(4) 1986, pp. 1002–1006.
Donahue et al., Blood 66(6) 1985, pp. 1479–1481.
Immunobiology of Natural Killer Cells, vol. I, 1986, ed. Lotzova et al., pp. 30–50, 90–102.
Shaw et al., *Cell. Immunol*, vol, 91, 1985, pp. 193–200.
Artaldo et al., *J. Exp. Med*. 164, ,1986, pp. 1193–1205.
Van de Griend et al., *J Immunology* vol. 136, 1986, pp. 1700–1707.
Lavier et al., *J Immunol* vol. 134, 1985, pp. 794–801.
Hogan et al., *J Immunal* vol. 135, 1985, pp. 1731–1738.
Sci. American, Medicine, vol. 1, 5:VIII (1987).
Civin et al., Exp. Hematol., 15:10 (1987).
Mageed et al., Cancer, 60:2913 (Dec. 15, 1987).
Tong et al., Blood, 70:1482 (Nov. 1987).
Ottow et al., Cancer, 60:1465(1987).
Hao et al., J. Immunol., 140:4042 (1988).

*Primary Examiner*—Garnette D. Draper
*Attorney, Agent, or Firm*—Robert M. Hallenbeck

[57] ABSTRACT

A method is disclosed for removing residual tumor cells from a patient with a neoplastic disorder by treating in vitro cell preparation with lymphokine activated cytotoxic cells.

13 Claims, 3 Drawing Sheets

METHOD OF PURGING RESIDUAL TUMOR CELLS IN VITRO WITH LYMPHOKINE ACTIVATED CYTOTOXIC CELLS

FIELD OF THE INVENTION

The present invention relates to a method for purging residual tumor cells from an in vitro cell preparation by treating it with lymphokine activated cytotoxic cells, and more particularly, relates to a method for purging in vitro tumor cells from an autologous hematopoietic progenitor (HP) enriched cell preparation by treating it with rIL-2 activated autologous NK cells.

BACKGROUND OF THE INVENTION

Leukemia is a type of cancer that affects blood cells (WBC). There are several types of leukemia each of which affect a specific WBC component. Among the WBC affected, for example, are B cells (e.g., acute lymphoblastic leukemia or "ALL") and granulocytes (e.g., acute myelogenous leukemia or "AML"). Typically, these leukemic cells are identified by (1) various morphological characteristics, (2) poor responsiveness to normal regulatory mechanisms, (3) reduced capacity for cell differentition and (4) the ability to suppress normal myeloid or lymphoid cell growth. For a more detailed, clinical description of leukemia and various forms it may take, see Scientific American, *Medicine*, vol. 1, 5:VIII (1987).

Among the currently prescribed treatment regimes for leukemia are total body irradiation and chemotherapy. The two treatment regimes, however, pose a clinical dilemma: because leukemia is a cancer of the blood, all of the cells in the blood and all of the cells that arise in bone marrow (and which then migrate to the blood) must be treated (i.e., destroyed or killed) in order to insure destruction of the neoplastic cells. Destruction of all these cells leaves the patient in a severely immunodepressed state which could be as fatal as the leukemia, and thus requires reconstituting the blood components. In such a case, the patient typically is given a marrow transplant or infusion to replace the components destroyed by the treatment.

In both bone marrow and in the blood, there are cells which are known as hematopoietic progenitor (HP) cells. These cells will differentiate in response to colony stimulating factors, and ultimately give rise to the various components of the blood (i.e., granulocytes, monocytes, lymphocytes etc.). Thus, HP cells are the cells of choice when reconstituting the hematopoietic system.

Preferably, HP cells from autologous bone marrow or peripheral blood would be used to reconstitute the hematopoietic system. The use of an autologous source avoids the serious complications, such as graft versus host disease, that arise when non-self tissues are used. A problem arises, however, when an autologous source is used because unless the HP cells are pure, residual tumor cells will isolate with the HP cells and the patient ultimately will relapse with neoplastic disease.

At least one method has been proposed to isolate pure HP cells. Civin et al. identified a monoclonal antibody (anti-My-10, ATCC HB-8483) which is specific for an HP cell surface antigen and may be used to isolate only HP cells from the patient's marrow. See Civin et al., Exp. Hematol., 15:10 (1987). This does nothing to the residual tumor cells in the marrow or blood but acts merely to purify the HP cell component.

Alternatively, it is known that there exists in the blood a subset of the lymphocyte population which will destroy certain tumor cells. This subset has been identified as natural killer (NK) cells. In addition to being effective against certain tumor cells, when activated by a lymphokine, these NK cells increase in their efficiency and range of tumors that can be killed. Recently, Rosenberg, in U.S. Pat. No. 4,690,915, has used lymphokine activated killer (LAK) cells in combination with recombinant interleukin-2 (rIL-2) to treat patients with certain solid tumors in vivo. Rosenberg states, however, that there are significant side effects to this method of treatment, and does not discuss or relate the method of treatment to the in vitro isolation and purification of autologous HP cells.

Accordingly, there has not been described a method for purging a cell preparation from a cancer patient of residual tumor cells using autologous, lymphokine activated cytotoxic cells.

BRIEF DESCRIPTION OF THE INVENTION

The present invention comprises a method to purge residual tumor cells from a cell preparation containing HP cells by treating the cell preparation with autologous, lymphokine activated cytotoxic cells in vitro. The cell preparation may be taken from autologous bone marrow or peripheral blood and further may be refined to enrich the HP cell component. The lymphokine may be an interleukin, such as rIL-2, or an interferon. The cytotoxic cells may be derived from bone marrow, peripheral blood, lymph node, lymphatics, spleen cells or thymus, and further may be refined to subfractions thereof.

DETAILED DESCRIPTION OF THE INVENTION

Figure 1A:
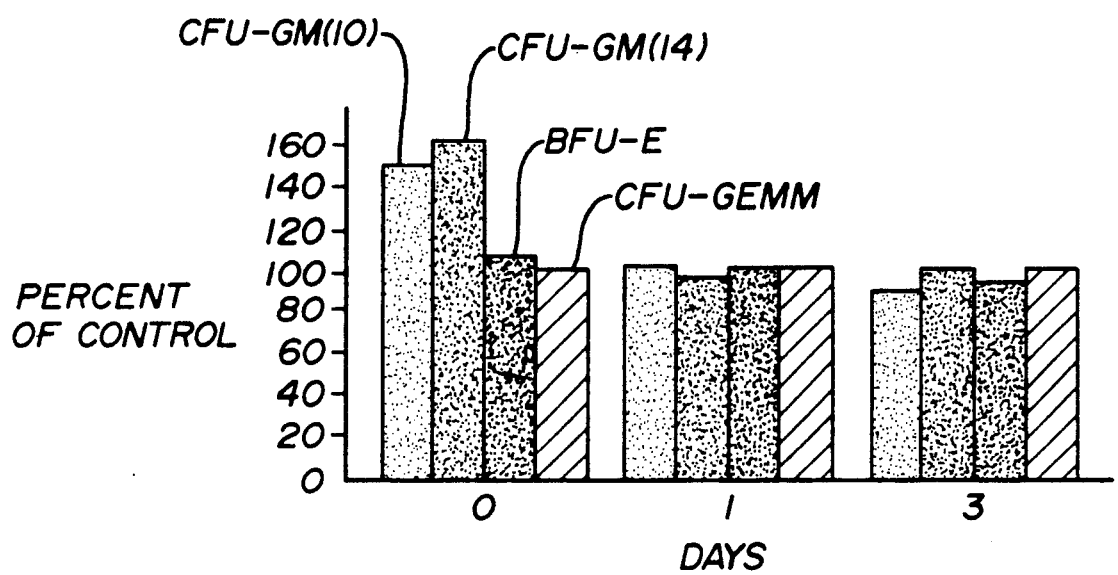
FIG. 1 comprises two bar graphs of days in culture with rIL-2 versus (A) percent of control for hematopoietic cell colony formation by low bouyant density cells (LBD) cultured with rIL-2 and (B) percent cytotoxicity for cytotoxic activity of LBD cells on tumor cell lines when cultured with rIL-2.

An autologous cell preparation is obtained from a patient suffering from a neoplastic disease. The cell preparation may be obtained from bone marrow or blood. The cell preparation must contain HP cells or cells sufficient to substantially repopulate and regenerate the patient's hematopoietic system.

While obtaining the cell preparation containing HP cells, a preparation of autologous cytotoxic cells is obtained. The source of cytotoxic cells may include blood, lymph nodes, lymphatics, spleen cells and thymus. The cytotoxic cells from these sources are selected based upon their ability to be activated by lymphokines to destroy residual tumor cells.

The lymphokines that will activate the cytotoxic cells may be selected from the group consisting of interleukins and interferons.

Once the cytotoxic cell preparation is obtained, it is exposed to an amount of lymphokine sufficient to activate the cytotoxic cells. The activated cytotoxic cells then are combined with the cell preparation for a time sufficient to destroy all residual tumor cells. Once depleted of residual tumor cell, the cell preparation may be reconstituted and returned to patient who has been treated by standard methods of irradiation, chemotherapy or any other method used to destroy tumor cells in vivo.

In the preferred embodiment, a cell preparation of peripheral blood mononuclear cells (PBMC) is isolated from a cancer patient induced into remission. A low buoyant density (LBD) fraction of PBMC is isolated to enrich the cell preparation for HP cells. This is done using discontinuous Percoll gradient centrifugation. HP cells (CD34+, as identified by the monoclonal antibody anti-HPCA-1, available from Becton Dickinson Immunocytometry Systems) usually comprise less than 2% of PBMC from normal peripheral blood and 4-10% of LBD cells. Alternatively, the cell preparation may be obtained by other methods which separate cells based upon size or bouyant density by standard techniques, such as leukophoresis.

LBD cells isolated from PBMC also comprise 45-60% NK cells (Leu19+, CD16+, CD3-) and 35-50% T cells (CD3+). In the preferred embodiment, therefore, the source of cytotoxic cells is co-isolated with the cell preparation. As such, recombinant Interleukin-2 (rIL-2) may be added directly to the cell preparation in amounts sufficient to activate the cytotoxic NK cells therein.

Upon treatment of the patient by irradiation, chemotherapy or by such other means as may be directed by the attending physician, the cell preparation which has been treated with lymphokine to activate the cytotoxic cells is returned to the patient in accordance with standard procedures.

The effectiveness of rIL-2 to activate NK cells and to destroy tumor cells without adversely affecting peripheral blood HP cells may be seen from the following examples.

PBMC were isolated from blood were depleted of monocytes and B cells by standard methods. LBD cells from PBMC were isolated by Percoll gradient centrifugation as described above. The presence of HP were cells in this cell preparation was confirmed by use of anti-HPCA-1. HP cells were sorted on a flow cytometer (FACStar TM, Becton Dickinson Immunocytometry Systems) as CD34+, and then were cultured in methylcellulose colony assays to determine the ability of the HP cells to differentiate. The results are set out in TABLE I.

TABLE I

| Donor | FACS Sorted | Hematopoietic Colony Formation by Peripheral Blood CD34+ Cells Colonies per $1.5 \times 10^5$ cells | | | |
|---|---|---|---|---|---|
| | | CFU-Gm(10) | CFU-Gm(14) | BFU-E | CFU-GEMM |
| #1 | CD34+ | 600 | 260 | 2400 | 18 |
| | CD34- | 1 | 1 | 4 | 0 |
| #2 | CD34+ | 532 | 248 | 2148 | ND |
| | CD34- | 1.2 | 1 | 4 | ND |
| #3 | CD34+ | 436 | 296 | 1828 | 84 |
| | CD34- | 0 | 0 | 0 | 0 |

Essentially, CD34+ cells were able to differentiate into granulocyte colony forming units (CFU-GM), erythrocyte burst forming units (BFU-E) and granulocyte, erythrocyte, monocyte and megakaryocyte colony forming units (CFU-GEMM). CD34- cells had no colony forming ability.

To investigate the effect of activated NK cells on HP cells from PBMC, LBD cells were incubated at 37° C. in the presence of rIL-2. At 0, 1 and 3 days, cells were plated for colony growth and assayed for activated NK cell cytotoxic activity against the NK sensitive tumor line K562 (erythromyeloleukemia, ATCC No. CCL 243) and the NK-resistant cell lines Daudi (B lymphoblastoid, ATCC No. CCL213) and Colo-205 (colon cancer, ATCC No. CCL 222).

Figure 1B:
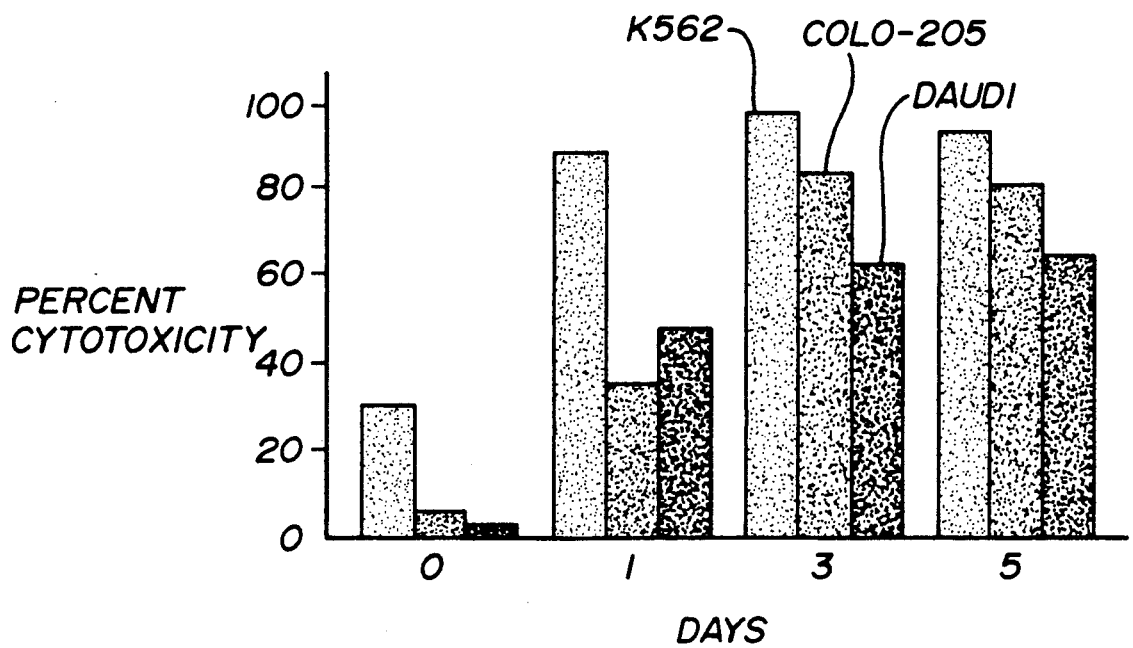
Figure 2A:
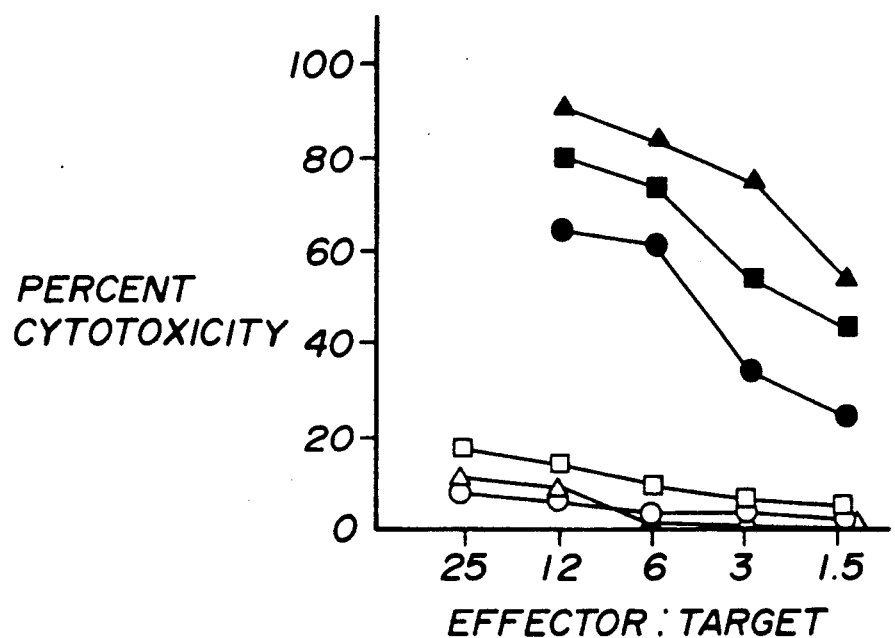
FIG. 2 comprises a series of plots of percent cytotoxicity versus effector:target ratios for rIL-2 unactivated (closed symbols) LBD on two uncultured tumor cell lines (o, Δ) and on the NK cell resistant colon carcinoma cell line Colo 205 (□).
Figure 2B:
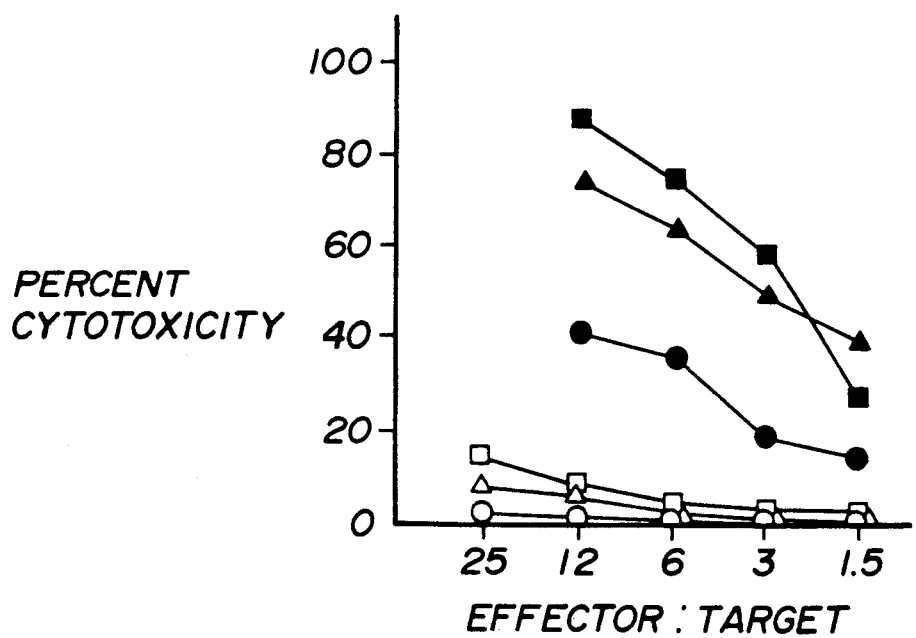
Figures 2C, 2D:
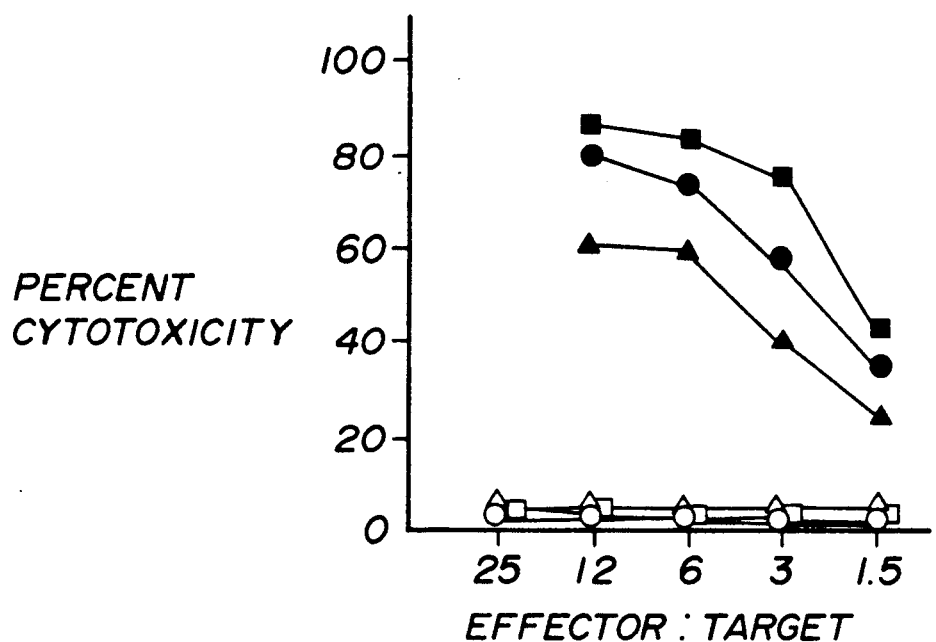

Referring to FIG. 1(A), culturing LBD cells for 3 days in the presence of rIL-2 had no inhibitory effects on the formation of hematopoietic colonies. Referring to FIG. 1(B), analysis of the cytotoxic activity of these LBD cell cultures clearly showed that the NK cells were substantially activated by 24 hours after culture with rIL-2 and reached maximal levels of cytotoxic potential by 3 days. Peripheral blood HP cells cultured more than 3 days with or without NK cells showed decreases in hematopoietic colony formation and viability.

Studies then were performed using PBMC derived from patients with acute myelogenous leukemia (AML) induced by chemotherapy into early remission. LBD cells were isolated from AML remission patients and examined for percentages of NK cells, T cells and CD34+ HP cells. These patients possessed normal percentages of NK cells and slightly elevated percentages of CD34+ HP cells. Referring to FIGS. 2A-D, the NK cells were functionally normal, and when activated overnight with rIL-2 demonstrated potent activated cytolysis against fresh uncultured AML tumor cells as well as the NK resistant solid tumor cell line, Colo-205 (FIGS. 3A-D).

CD34+ HP cells from the LBD cells of AML remission patients also demonstrated the ability to form normal CFU-GM, BFU-E and CFU-GEMM hematopoietic colonies in vitro. rIL-2 activated NK cells from most AML patients were also capable of efficiently lysing autologous AML tumor cells (Table 2).

TABLE 2

| Lysis of Autologous Tumor by rIL2 Activated NK Cells from AML Patients Tumor Targets Percent Cytotoxicity | | | | | | | |
|---|---|---|---|---|---|---|---|
| Effector Cell Source Patient | E:T | K562 | Colo | AML-1 | AML-2 | AML-3 | AML-4 |
| AML-1 | 6 | 73 | 69 | 69 | 21 | — | — |
| | 3 | 76 | 58 | 55 | 10 | | |
| | 1.5 | 68 | 41 | 43 | 7 | | |
| AML-2 | 6 | 90 | 60 | 67 | 32 | — | — |
| | 3 | 65 | 32 | 53 | 27 | — | — |
| | 1.5 | 47 | 23 | 24 | 14 | — | — |
| AML-3 | 6 | 85 | 67 | — | 22 | 11 | — |
| | 3 | 61 | 50 | — | 14 | 5 | — |
| | 1.5 | 60 | 36 | — | 10 | 1 | — |
| AML-4 | 6 | 92 | 65 | — | 52 | — | 76 |
| | 3 | 90 | 53 | — | 40 | — | 63 |
| | 1.5 | 86 | 40 | — | 25 | — | 51 |

In these studies, PBMC from AML patients with varied percentages of tumor blasts were incubated in the presence of rIL-2 for 10-14 days. NK cells then were purified from these cultures using a FACStar TM flow cytometer and analyzed for cytolytic capabilities against a panel of tumor cells including autologous uncultured tumor, and fresh uncultured allogeneic AML tumors. In three of the four patients studies, rIL-2 activated NK cells were very cytolytic against autologous AML tumor as well as allogeneic AML tumor, Colo-205, and K562. Patient AML-3 demonstrated strong levels of cytolytic activity against Colo-205, however, showed low levels of killing against autologous or allogeneic AML tumor cells.

These and other embodiments of the invention may suggest themselves to those skilled in the art. Accordingly, this disclosure should not be taken in a limiting sense.

What is claimed is:

1. In a method of transplantation of an autologous cell preparation that is enriched for human progenitor cells, the improvement comprising the steps of:
    (a) obtaining a preparation of autologous cytotoxic cells;
    (b) activating said cytotoxic cells in vitro with IL-2; and
    (c) combining said activated cytotoxic cells with said enriched progenitor cell preparation.

2. The method of claim 1 wherein the cell preparation is derived from bone marrow.

3. The method of claim 1 wherein the cell preparation is derived from peripheral blood.

4. The method of claim 1 wherein the cell preparation is enriched for human progenitor cells by separation procedures based on cell size or the presence of certain cell surface antigens.

5. The method of claim 1 wherein the cytotoxic cells are obtained from the cell preparation.

6. The method of claim 1 wherein the cytotoxic cells are derived from an autologous source selected from the group consisting of peripheral blood, lymph node, lymphatics, thymus, bone marrow and spleen.

7. The method of claim 6 wherein the cytotoxic cells are derived from peripheral blood.

8. The method of claim 7 wherein the cytotoxic cells derived from peripheral blood are NK cells.

9. In a method of transplantation of an autologous cell preparation that is enriched for human progenitor cells, the improvement comprising the steps of:
    (a) obtaining a preparation of autologous NK cells;
    (b) activating said NK cells in vitro with IL-2; and
    (c) combining said IL-2 activated NK cells with said enriched progenitor cell preparation.

10. The method of claim 9 wherein the cell preparation is enriched for progenitor cells by separation procedures based upon the presence of the CD34 antigen.

11. The method of claim 9 wherein the NK cells are obtained from the cell preparation.

12. The method of claim 9 wherein the cell preparation is derived from bone marrow.

13. The method of claim 9 wherein the cell preparation is derived from peripheral blood.

* * * * *